(12) United States Patent
Nicolella et al.

(10) Patent No.: US 9,039,784 B2
(45) Date of Patent: May 26, 2015

(54) MICRO-STRUCTURE PARTICLES FOR LOAD BEARING BONE GROWTH

(75) Inventors: Daniel P. Nicolella, San Antonio, TX (US); Nitin Nitin, Vacaville, CA (US); Heather S. Hanson, San Antonio, TX (US); Kwai S. Chan, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 670 days.

(21) Appl. No.: 12/510,582

(22) Filed: Jul. 28, 2009

(65) Prior Publication Data

US 2011/0029026 A1 Feb. 3, 2011

(51) Int. Cl.
| | |
|---|---|
| *A61F 2/28* | (2006.01) |
| *A61F 2/30* | (2006.01) |
| *A61L 27/40* | (2006.01) |
| *A61L 27/44* | (2006.01) |
| *A61L 27/46* | (2006.01) |
| *A61L 27/12* | (2006.01) |

(Continued)

(52) U.S. Cl.
CPC ............ *A61F 2/28* (2013.01); *A61F 2210/0085* (2013.01); *A61L 27/40* (2013.01); *A61L 27/10* (2013.01); *A61L 27/446* (2013.01); *A61L 27/042* (2013.01); *A61L 27/12* (2013.01); *A61L 27/46* (2013.01); *A61L 2400/06* (2013.01); *A61L 2400/12* (2013.01); *A61F 2/30907* (2013.01); *A61F 2002/30738* (2013.01); *A61F 2002/30588* (2013.01); *A61F 2/30734* (2013.01); *A61F 2002/30583* (2013.01); *A61F 2002/30919* (2013.01); *A61F 2/2846* (2013.01); *A61F 2002/2817* (2013.01); *A61F 2002/30062* (2013.01); *A61F 2002/30079* (2013.01); *A61F 2002/30235* (2013.01); *A61F 2002/3092* (2013.01); *A61F 2210/0004* (2013.01); *A61F 2210/009* (2013.01); *A61F 2230/0069* (2013.01)

(58) Field of Classification Search
CPC ... A61F 2/30767; A61F 2/30965; A61F 2/28; A61F 2/0063
USPC ............ 623/23.75, 23.52, 23.6, 23.73, 23.76
See application file for complete search history.

(56) References Cited

U.S. PATENT DOCUMENTS

| | | | | |
|---|---|---|---|---|
| 4,629,464 | A | * | 12/1986 | Takata et al. ................ 623/23.61 |
| 5,344,640 | A | * | 9/1994 | Deutsch et al. .............. 424/9.32 |

(Continued)

OTHER PUBLICATIONS

AZ Nanotechnology, "Carbon Nanotubes Can Serve As Scaffolds for New Bone Growth," available at www.azonano.com/news.asp?newsID=1155 ; retrieved on Dec. 11, 2008 (4 pages).

(Continued)

*Primary Examiner* — Andrew Iwamaye
*Assistant Examiner* — Leslie Lopez
(74) *Attorney, Agent, or Firm* — Grossman, Tucker et al (57) ABSTRACT

The present disclosure relates to methods of facilitating bone growth. The method may include positioning a device around at least a portion of a bone exhibiting a defect, the device capable of retaining bone segments and micro-structured particles. The method may also include applying micro-structure particles within the device to the defect, wherein each of the micro-structure particles include at least one pore therein. In addition, the method may include aligning at least a portion of the micro-structure particles and applying a polymer to the particles and solidifying the polymer.

6 Claims, 6 Drawing Sheets

(51) Int. Cl.
*A61L 27/10* (2006.01)
*A61L 27/04* (2006.01)

(56) References Cited

U.S. PATENT DOCUMENTS

| | | | |
|---|---|---|---|
| 5,422,340 A * | 6/1995 | Ammann et al. | 424/489 |
| 2001/0020188 A1 * | 9/2001 | Sander | 623/23.57 |
| 2003/0009235 A1 * | 1/2003 | Manrique et al. | 623/23.63 |
| 2005/0112397 A1 * | 5/2005 | Rolfe et al. | 428/593 |
| 2005/0240281 A1 | 10/2005 | Slivka et al. | |
| 2006/0184246 A1 * | 8/2006 | Zwirkoski | 623/11.11 |
| 2007/0151202 A1 | 7/2007 | Cox et al. | |
| 2008/0138602 A1 | 6/2008 | Canham et al. | |
| 2008/0206297 A1 * | 8/2008 | Roeder et al. | 424/422 |

OTHER PUBLICATIONS

Materials Research Society, "Controlled Release of Bone Growth Factors from Injectable Biodegradable Polymer Scaffolds for Bone Tissue Engineering," available at http://www.mrs.org/s_mrs/sec_subscribe.asp? CID=2424&DID=137466&action=detail; retrieved on Dec. 11, 2008 (2 pages).

E! Science News, "Hydrogels provide scaffolding for growth of bone cells," available at http://esciencenews.com/articles/2008/08/17/hydrogels.provide.scaffolding.growth.bone.cells; retrieved on Dec. 11, 2008 (1 page).

Mahony, Jr., "Porous bioactive nanostructured scaffolds for bone regeneration: a sol-gel solution," available at http://www.ncbi.nlm.nih.gov/pubmed/18373428; retrieved on Dec. 11, 2008 (1 page).

AZ Materials, "Bioceramics—An overview including calcium phosphates, hydroxyapatite, Alumina, Zirconia and Pyrolytic Carbon," available at http://www.azom.com/details.asp?ArticleID=1743; retrieved on Dec. 18, 2008 (4 pages).

Blokhuis, et al., "Resorbable calcium phosphate particles as a carrier material for bone marrow in an ovine segmental defect," Abstract available at http://cat.inist.fr/?aModele=afficheN&cpsidt=1414739; retrieved on Dec. 18, 2008 (2 pages).

All Academic Research, "Polymer-Ceramic Scaffolds for Guiding Bone Growth Around Dental Implants," available at http://www.allacademic.com/meta/p_mla_apa_research_citation/1/8/5/3/6/p185364_index.html; retrieved on Dec. 11, 2008 (2 pages).

\* cited by examiner

MICRO-STRUCTURE PARTICLES FOR LOAD BEARING BONE GROWTH

FIELD OF THE INVENTION

The present disclosure relates to micro-structure particles for bone growth and, in particular, for load bearing bone growth, wherein the micro-structure particles may include features which may align along a given axis.

BACKGROUND

Bone defects, such as the breakage or fracture of bones, may require the use of various fixation devices to align the bone pieces in a manner which may facilitate healing. For example, a variety of plates, screws, pins and/or wires, may be utilized to fix or stabilize bone fragments. However, in some cases, the use of such devices may cause additional fractures, infection or necrosis. Furthermore, additional procedures may be necessary to further the healing process, such as to elongate the bone or to remove plates, screws, or other devices.

SUMMARY OF THE INVENTION

An aspect of the present disclosure relates to a method of facilitating bone growth. The method may include positioning a device around at least a portion of a bone exhibiting a defect, the device capable of retaining bone segments and micro-structured particles. The method may also include applying micro-structure particles within the device to the defect, wherein each of the micro-structure particles include at least one pore therein. In addition, the method may include aligning at least a portion of the micro-structure particles and applying a polymer to the particles and solidifying the polymer.

Another aspect of the present disclosure relates to a method of facilitating bone growth. The method may include positioning a device substrate, including micro-structure particles and a polymer disposed thereon, around at least a portion of a bone exhibiting a defect, wherein the device may be capable of retaining bone segments and the micro-structured particles, wherein each of the micro-structure particles may include at least one pore therein. The method may also include aligning at least a portion of the micro-structure particles.

A further aspect of the present disclosure related to a method for facilitating bone growth, wherein the method may include applying a first polymer including micro-structure particles within a defect, wherein each of the micro-structure particles may include at least one pore therein and the first polymer may exhibit a viscosity of 50,000 centipoise to 500,000 centipoise. The method may also include aligning at least a portion of the micro-structure particles and applying a second polymer to the first polymer and solidifying a portion of the first polymer, forming a shell around at least a portion of a defect in a bone segment. The shell may be capable of retaining the bone segment and micro-structured particles.

BRIEF DESCRIPTION OF THE DRAWINGS

The above-mentioned and other features of this disclosure, and the manner of attaining them, will become more apparent and better understood by reference to the following description of embodiments described herein taken in conjunction with the accompanying drawings, wherein.

DETAILED DESCRIPTION

The present disclosure relates to a method and system for treatment. The method and system may include the implantation of a material or series of materials that may provide load bearing strength within a relatively short period of time, a day to a few weeks, and provide for the promotion of growth of new bone tissue.

Figure 1:
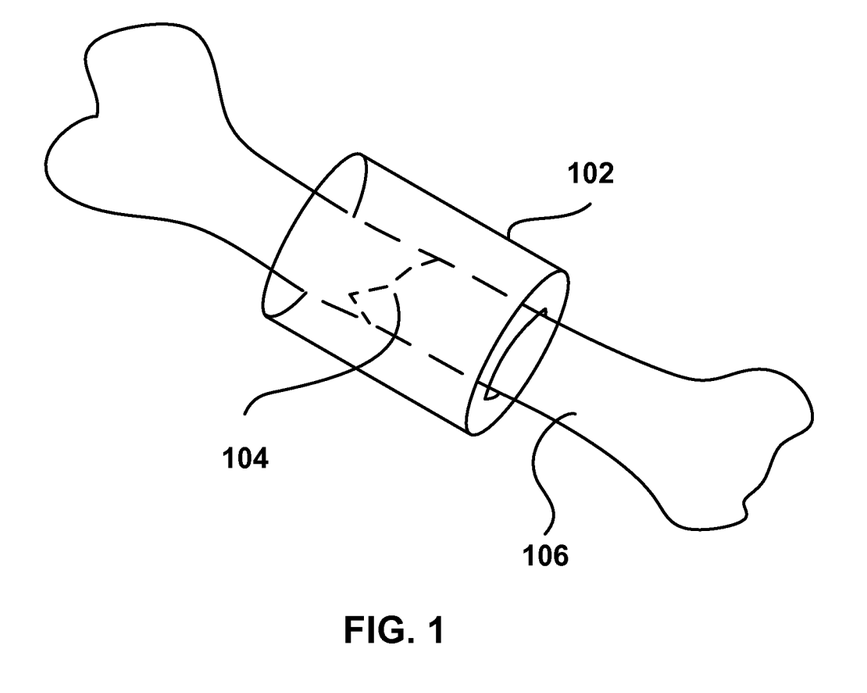
FIG. 1 is an example of a tubular device positioned over a bone fracture.

The system may include a relatively tubular device, which may be positioned around a fracture, breakage or other defect in a bone. FIG. 1 illustrates an example of a tubular device 102 positioned over a bone fracture 104 in a bone 106. The tubular material may be formed of a polymer material. The polymer material may be bioresobable, which may be understood as the ability of the material to be hydrolyzed or enzymatically degraded, such as enzymatic degradation within a given patient (human or animal). Examples of bioresobable materials may include polyurethanes, polycaprolactones, poly(lactic acid), poly(glycolic acid), etc.

Figure 2:
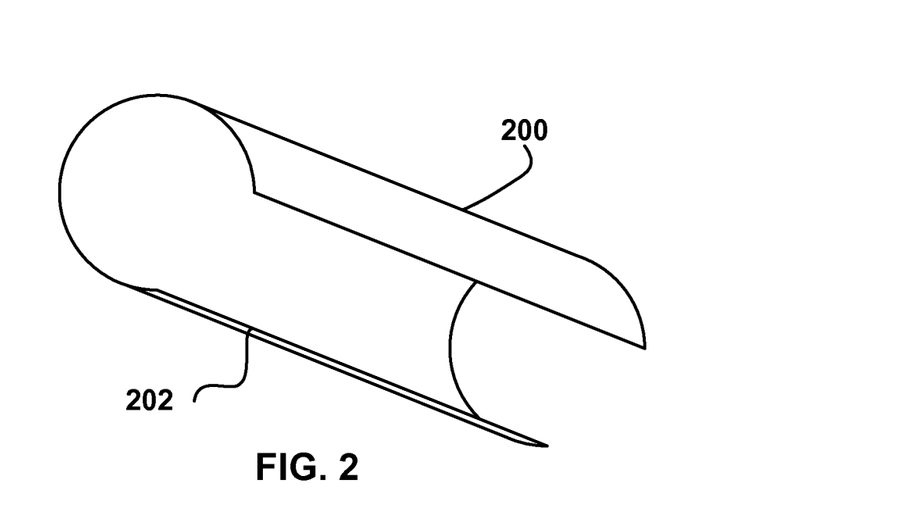
FIG. 2 is an example of a flexible sheet that may be utilized as a tubular device.

The tubular device may be provided as a relatively flexible sheet and curved around the bone segment or, as illustrated in FIG. 2, the tubular device 200 may be provided in an arcuate form having a longitudinal slit 202 allowing the passage of the bone segment therethrough. In one example, the tubular device may fit around the bone and seal onto itself via mechanical or chemical means. For example, one may utilize a bioresorbable adhesive. In another example, the tubular device may be attached to one or more bone segments also via mechanical or chemical means, such as through the use of screws, pins or other retention devices, or by an adhesive, such as bone cement.

Figure 3:
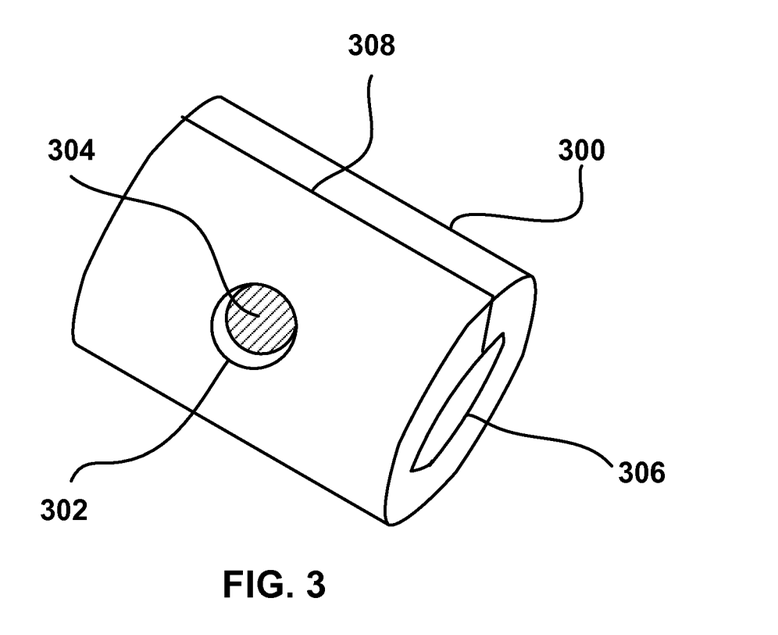
FIG. 3 is an example of a tubular device including an injection port.

As illustrated in FIG. 3, the tubular device 300 may include an injection port 302. The injection port may be an opening defined through the wall of the tubular device. In some examples, the opening may include a self sealing membrane 304, such as one formed from silicone, polybutadiene, etc. Furthermore, in some examples, the injection port may be raised from the tubular device.

Once affixed, the tubular device may be filled with micro-structure particles. The micro-structure particles may include cylindrical, spherical, elliptical or other multifaceted particles, including those which may be hexagonal, octagonal, etc. The particles may have a length of 50 to 5000 µm, including all values and increments therein in 1.0 µm increments.

The particles may also have a diameter (largest cross-sectional length) of 60 µm to 2000 µm, including all values and increments therein, in 1.0 µm increments. The particles may be formed from a relatively rigid bone-like material, such as calcium-phosphate, including amorphous calcium phosphate, dicalcium phosphate, α-tricalcium phosphate, β-tricalcium phosphate, pentacalcium hydroxyl apatite, and/or tetracalcium phosphate monoxide. In addition, the particles may be formed from a material that may be resorbable, inert or active (i.e., capable of actively taking part in physiological processes). The particles may be coated with a growth factor material, such as vascular endothelial growth factor (VEGF), statins, bone morphogenic proteins such as BMP-2 or with a relatively quickly resorbable polymer, inorganic or composite material such as collagen, poly(lactic-glycolic acid), poly(caprolactone), calcium phosphate, as well as polymer-inorganic composites such as biomineralized collagen-calcium phosphate.

The micro-structure particles may include one or more pores. It may be appreciated that the pores may allow for the growth of tissue therein. The pores may have a diameter in the range of 50 µm to 1,000 µm, including all values and increments therein, such as 100 µm to 500 µm. In some examples, the pores may be channels extending through the micro-structure particles, which extend along an axis of the particle. It may be appreciated that when the micro-particles align, the pores may align as well, forming a channel that spans across the micro-structure particles.

The pores may also be filled with one or more growth factors material, such those which may be osteogenic or angiogenic. Osteogenic growth factors may be understood as growth factors (compounds) that promote bone growth. Angiogenic growth factors may be understood as factors (compounds) that promote blood vessel growth. Such growth factors may include as vascular endothelial growth factor (VEGF), statins, bone morphogenic proteins such as BMP-2 or the pores may be filled with a relatively quickly resorbable polymer, inorganic or composite material such as collagen, poly(lactic-glycolic acid), poly(caprolactone), calcium phosphate, as well as polymer-inorganic composites such as biomineralizes collagen-calcium phosphate.

Figure 4:
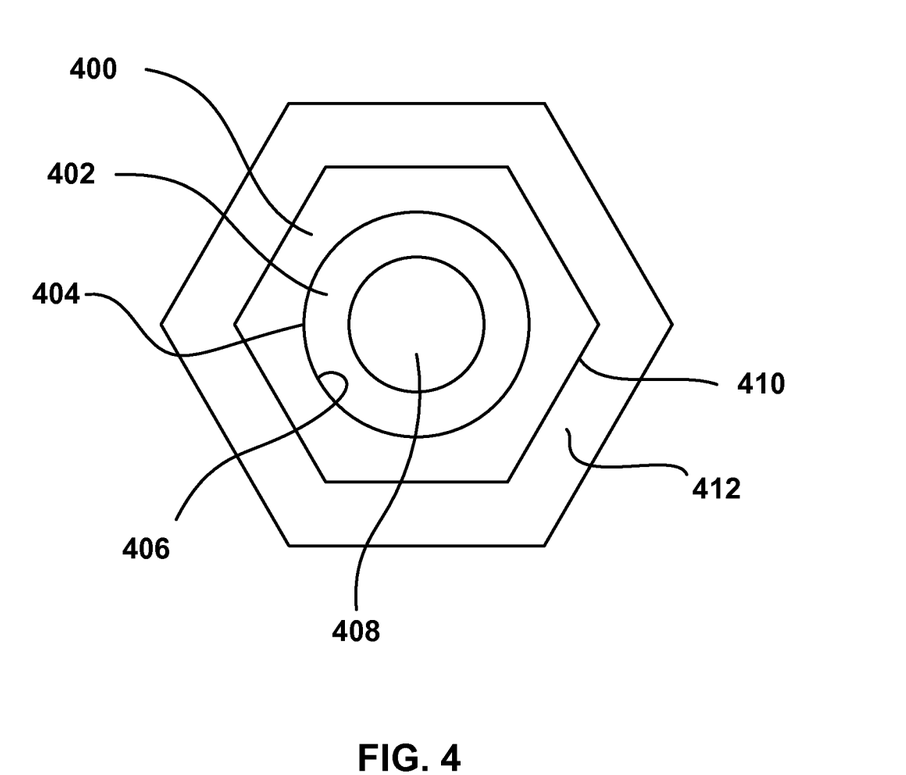
FIG. 4 illustrates an example of a microstructure particle.

A contemplated example of a micro-structured particle is illustrated in FIG. 4. The particle 400 may be formed of calcium phosphate or a biopolymer composite cement and may include an osteogenic growth factor 402 coated within a pore 404, on the pore surface 406, of the particle. In addition, an angiogenic growth factor 408 may be provided within the pore 404. It may be appreciated that the growth factors employed within the pore may be arranged in any desired configuration. For example, at 408 one may incorporate osteogenic growth factor and at 402 one may incorporate angiogenic growth factor. Furthermore, the surface of the particle 410 may be coated with coating 412 including a functionalized polymer (such as poly(lactic acid), poly(glycolic acid), poly(caprolactone), an iron oxide or other ferrous composite, etc. The use of iron oxide or other ferrous composite materials may be selected to provide magnetic characteristics, as explained more fully below.

Figure 5A:
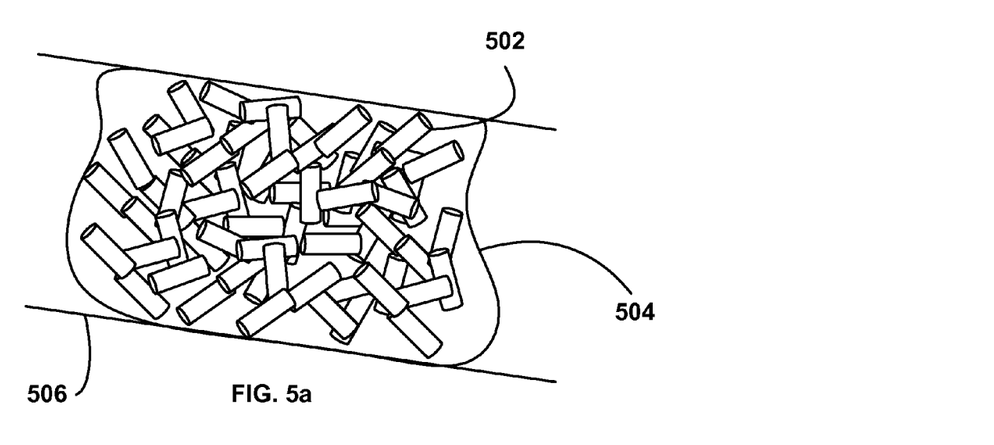
FIG. 5a illustrates unaligned microstructure particles injected into a bone defect.
Figure 5B:
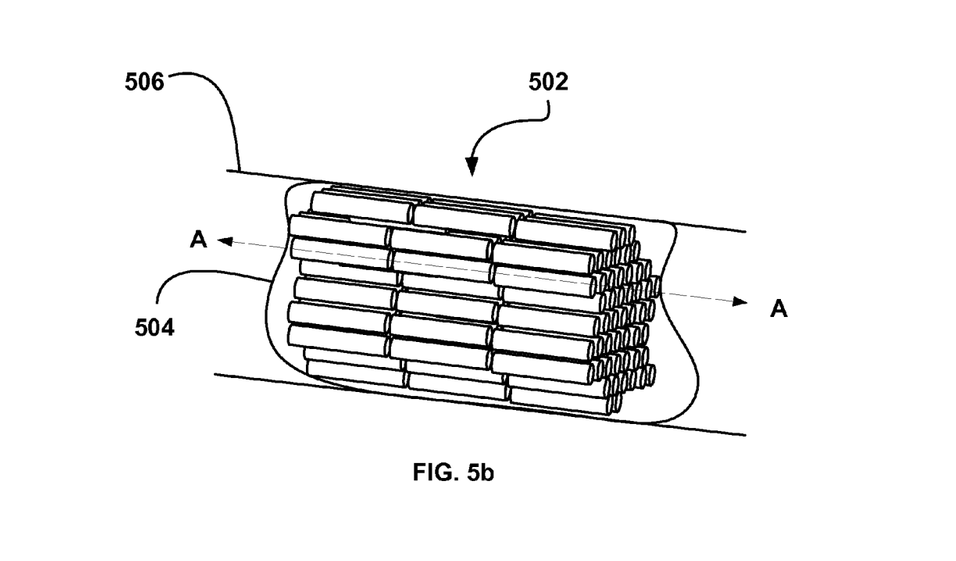
FIG. 5b illustrates the microstructure particles of FIG. 5a in an aligned arrangement.

That is, the micro-structure particles may include self-alignment features, wherein the micro-structure particles may align in a relatively uniform manner when at a targeted location in a patient, such as at a bone fracture site. For example, the particles may include magnetic polarization, electrically conducting or chemical alignment features. The particles may be aligned by vibration, magnetic fields, electrical fields or flotation. Furthermore, alignment of the micro-particles may form an interconnected pore structure. Alignment may also provide for compaction of the particles. FIG. 5a illustrates an example of relatively random particle alignment upon injecting or placing the micro-structure particles 502 proximate to or into the bone defect 504 in a bone 506. FIG. 5b illustrates and example of the particles 502 once at least a portion or all of the particles are aligned in the bone defect 504 within the bone 506. As illustrated in FIG. 5b, the particles may align along a given axis (A-A) of the bone, which may in some examples include alignment with a given bone length dimension.

Prior to or after the alignment of the micro-structure particles, other secondary particles including growth factors or calcium-phosphate may be added to the tubular device to fill in any voids. In addition, a polymer may be added to adhere the micro-structure particles and secondary particles (if present) together, within the tubular device. The polymer may include, but is not limited to, gelatin, collagen, poly(caprolactone), etc. The polymer may be provided as a liquid, or in liquid form, i.e., the polymer may exhibit a relatively low viscosity. That is, the viscosity may be less than or equal to 500,000 centipoise, e.g. in the range of 50,000 centipoise to 500,000 centipoise, including all values and increments therein.

The polymer may then be cured or at least partially solidified by the addition of a cross-linking agent, exposure to light, including UV light exhibiting at least one wavelength in the range of 400 nm to 10 nm, heat curing or a combination thereof. At least partially solidified may be understood as a state wherein the liquid polymer may resist, to some degree, deformation and/or changes in volume, and exhibit an increase in viscosity.

The tubular device may be sealed before or after adding the various particles or, in some examples, the tubular device may be removed. Referring back to FIG. 3, the tubular device may be sealed at an edge 306 or along the length of adjoining surfaces 308 of the device. Sealing may occur by the use of mechanical or chemical means, such as bending the tubular device or the addition of an adhesive or cement. For example, as alluded to, the tubular device may be bent into a cylinder and secured utilizing the mechanical means described above. A cement or adhesive, such as bone cement or cyanoacrylate may be applied to seal the edges as well.

Figure 6A:
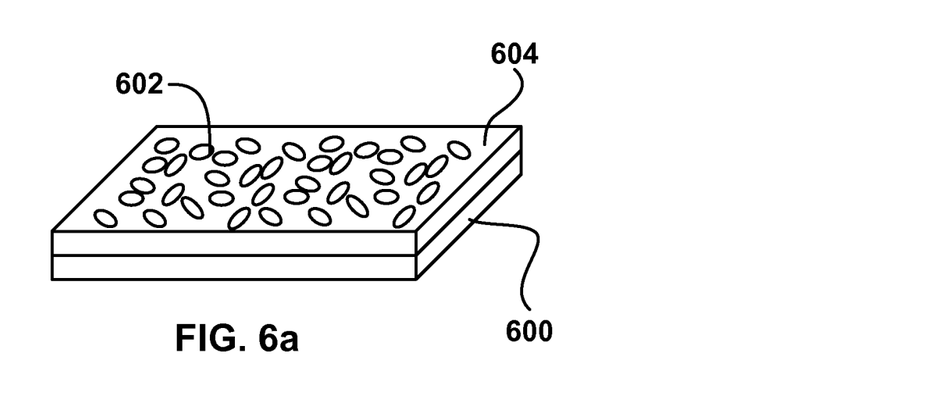
FIG. 6a illustrates unaligned microstructure particles disposed on a sheet in a polymer matrix, wherein the resin sheet may be formed into a tubular device over a bone segment.
Figure 6B:
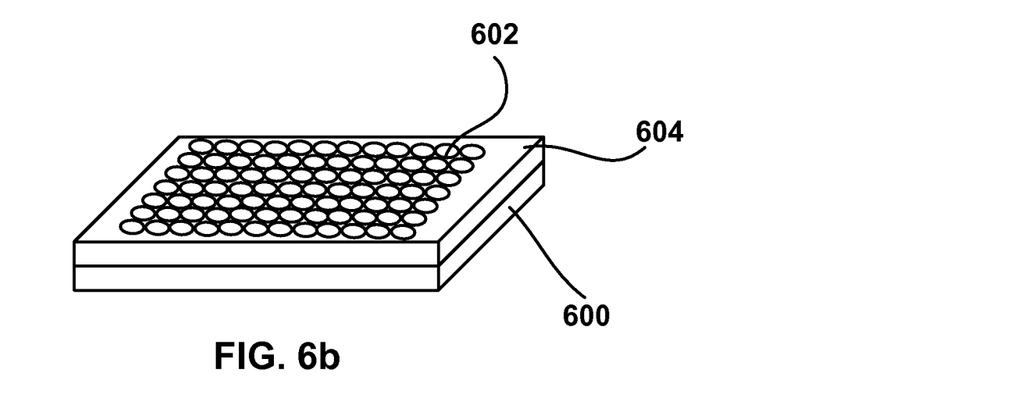
FIG. 6b illustrates aligned microstructure particles disposed on a sheet in a polymer matrix, wherein the resin sheet may be formed into a tubular device over a bone segment.

In other examples, a tubular device may be provided as a substrate in the form of, for example, a sheet, as illustrated in FIG. 6a. The substrate 600 may include a biocompatible material or a reinforcing composite, such as those described above. The micro-structure particles 602 may be placed on a tubular device substrate 600 and a polymer 604 may be added to the particles spread on the sheet. The polymer may include, but is not limited to, gelatin, collagen, poly(caprolactone), or other polymers or polymer-precursors. The sheet may then be cut or otherwise adjusted to size, wrapped around the fracture, break or defect point of the bone, supported by viable bone segments and secured in place, forming a tubular device in which the micro-structure porous network may be contained. If not already polymerized prior to application of the sheet to the bone, the polymer may then be polymerized or cross-linked. Furthermore, the tubular device may be removed from the bone once polymerization or cross-linking begins. It may be appreciated that the micro-structure particles 602 may be aligned before, as illustrated in FIG. 6b, or after placement of the sheet around the viable bone segments and formed into a tubular structure.

Figure 7A:
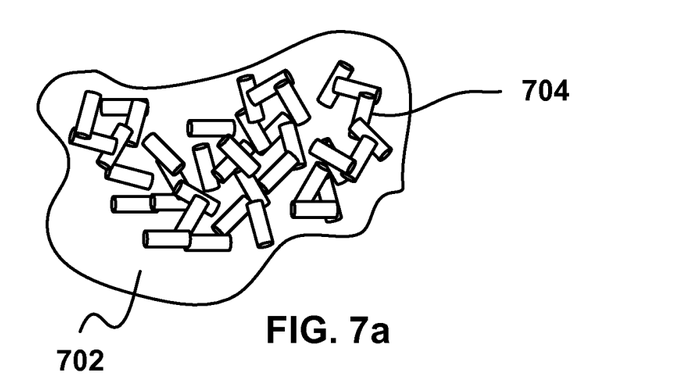
FIG. 7a illustrates microstructure particles in a polymer material.
Figure 7B:
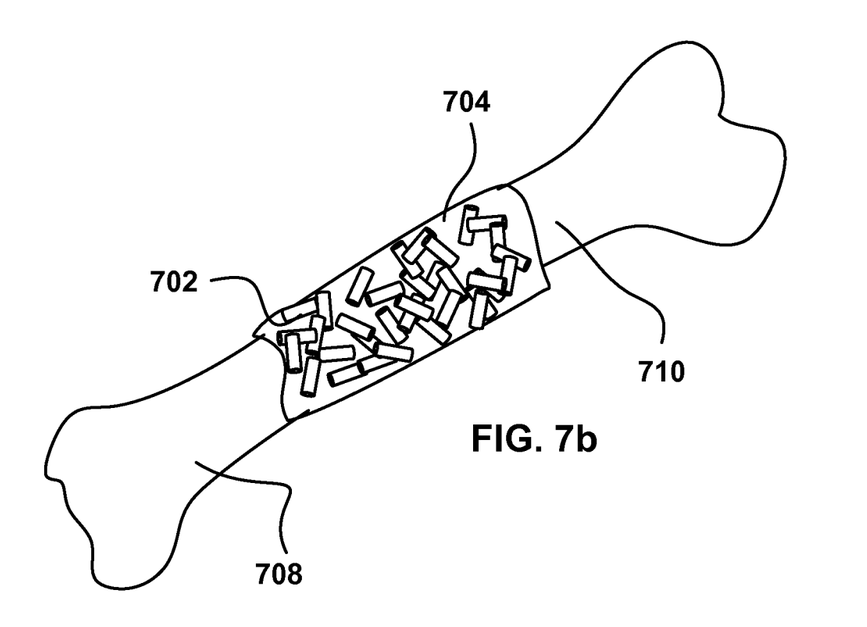
FIG. 7b illustrates the microstructure particle/polymer material composition positioned within a bone defect between two bone segments.

In a further example, illustrated in FIG. 7a, micro-structural particles 702 may be encapsulated or otherwise compounded with a polymer material or polymer pre-cursor 704. The mixture may exhibit a semi-solid viscosity, i.e., the material may be substantially solid but plastically deformable upon the application of pressure. As alluded to above, the viscosity of the polymers utilized for the mixture may be in the range of 50,000 centipoise to 500,000 centipoise. As illustrated in FIG. 7b, the mixture of the micro-structural particles 702 and the polymer material 704 may then be implanted between viable bone segments 708, 710. A liquid polymer may then be added around the mixture of the micro-structural particles and encapsulating material, which may then be cross-linked providing a relatively rigid shell around a relatively soft core of the mixture of the micro-structural particles and encapsulating material. The liquid polymer may include, for example, functionalized acrylate monomers. The micro-structure particles may be aligned and the core may be polymerized as well.

The tubular devices formed herein may provide a degree of mechanical support for the bone. In addition, the micro-structure particles may also form some degree of stability and support for the bone. It may be appreciated that the micro-structure particles may also form support for the growth of tissue, which may grow around the particles and/or within any pores. More specifically, it can be appreciated that alignment of particles along the length of a given bone, as illustrated in FIG. 5b, when contained within tubular device 102 illustrated in FIG. 1, will provide stability and support for the underlying bone during a given healing period.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. A method of facilitating bone growth in a patient having a site of a bone fracture with bone segments, comprising:
    positioning a flexible tubular device comprising a bioresorbable polymer material, said positioning being at the site of the bone fracture and around an external surface of the bone fracture;
    affixing the flexible tubular device to the bone segments to retain the bone segments and form an affixed device at the site of the bone fracture;
    filling micro-structure particles into said affixed device so as to apply said micro-structure particles to said fracture, wherein each of said micro-structure particles has a longitudinal axis and include a first pore extending through an entire thickness of said micro-structure particles along the longitudinal axis, said first pore having a diameter in the range of 50 μm to 1,000 μm;
    aligning at least a portion of said micro-structure particles within said affixed device at the site of the bone fracture along their longitudinal axes into a plurality of rows such that:
        each row comprises a plurality of said micro-structure particles; and
        first pores of adjacent micro-structure particles in each row are aligned so as to provide an interconnected pore structure forming a channel spanning across and through the plurality of said micro-structure particles;
    applying a filler polymer having a viscosity of less than or equal to 500,000 centipoise to said aligned micro-structure particles at the site of the bone fracture; and
    solidifying said polymer at the site of the bone fracture.

2. The method of claim 1, wherein said bioresorbable polymer material is selected from one or more of the following materials: polyurethanes, polycaprolactones, poly(lactic acid), and poly(glycolic acid).

3. The method of claim 1, wherein said micro-structure particles comprise a calcium phosphate based material.

4. The method of claim 1, further comprising coating said micro-structure particles with a growth factor.

5. The method of claim 1, wherein said micro-structure particles include a ferrous composite material coated on said micro-structure particles.

6. The method of claim 5, wherein said aligning said micro-structure particles and first pores of adjacent micro-structure particles in each of said rows comprises aligning with a magnetic field.

\* \* \* \* \*